United States Patent
Nonaka et al.

(10) Patent No.: US 8,736,274 B2
(45) Date of Patent: May 27, 2014

(54) METHOD AND APPARATUS FOR DIAGNOSING ELECTROCHEMICAL SENSOR

(75) Inventors: Atsushi Nonaka, Nishinomiya (JP); Hisao Ohnishi, Osaka (JP); Hidemasa Nonaka, Osaka (JP); Toshiro Nakayama, Itami (JP); Tomohiro Inoue, Hyogo (JP); Yuki Kato, Mino (JP)

(73) Assignees: Osaka Gas Co., Ltd., Osaka (JP); Figaro Engineering Inc., Osaka (JP)

( * ) Notice: Subject to any disclaimer, the term of this patent is extended or adjusted under 35 U.S.C. 154(b) by 507 days.

(21) Appl. No.: 13/094,374

(22) Filed: Apr. 26, 2011

(65) Prior Publication Data

US 2012/0274337 A1 Nov. 1, 2012

(51) Int. Cl.
*G01R 31/08* (2006.01)
*G01R 27/08* (2006.01)

(52) U.S. Cl.
USPC ............................. 324/525; 324/691

(58) Field of Classification Search
USPC .................................. 324/525, 691
See application file for complete search history.

(56) References Cited

U.S. PATENT DOCUMENTS

| 6,200,443 | B1 | 3/2001 | Shen et al. |
| 2004/0091759 | A1* | 5/2004 | Harrington et al. ............. 429/22 |
| 2004/0221641 | A1* | 11/2004 | Moritsugu et al. ............ 73/23.31 |
| 2005/0121338 | A1 | 6/2005 | Inoue |
| 2007/0259256 | A1* | 11/2007 | Le Canut et al. ............... 429/90 |

FOREIGN PATENT DOCUMENTS

| JP | 2000146908 A | 5/2000 |
| JP | 2004279293 A | 10/2004 |
| JP | 2008164309 A | 7/2008 |

* cited by examiner

*Primary Examiner* — Amy He
(74) *Attorney, Agent, or Firm* — The Webb Law Firm

(57) ABSTRACT

A method and apparatus for diagnosing an electrochemical sensor that detects the concentration of a gas are operative for diagnosing whether or not the sensor is in an error state due to a rise in a resistance in the electrolyte of the sensor. Such detection is made on the basis of a current flowing between a sensing electrode and an opposite electrode or a voltage corresponding to the current. A method for diagnosing an electrochemical sensor having a solid or liquid electrolyte between a sensing electrode and an opposite electrode detects the concentration of the gas to be detected on the basis of a current flowing between the sensing electrode and the opposite electrode, or a voltage corresponding to the current. Whether or not the electrochemical sensor is in an error state is diagnosed on the basis of a resistance of the electrolyte between the two electrodes of the electrolyte.

12 Claims, 6 Drawing Sheets

Fig.1

METHOD AND APPARATUS FOR DIAGNOSING ELECTROCHEMICAL SENSOR

BACKGROUND OF THE INVENTION

1. Field of the Invention

The present invention relates to a diagnostic method for diagnosing an electrochemical sensor provided with a solid or liquid electrolyte between a sensing electrode for contacting a gas to be detected and an opposite electrode and designed for detecting the concentration of the gas to be detected on the basis of a current flowing between the sensing electrode and the opposite electrode or a voltage corresponding to this current, and to an electrochemical sensor diagnostic apparatus.

2. Description of the Related Art

An electrochemical sensor usually comprises a sensing electrode and an opposite electrode having an electrolyte solution or a solid electrolyte in between, and is configured to enable detection of the concentration of a gas to be detected in accordance with an output of a current generated by the sensing electrode oxidizing the gas to be detected or a voltage corresponding to this current (hereafter sometimes simply called current for short). An example of this electrochemical sensor is a CO sensor for detecting carbon monoxide gas or the like as the gas to be detected.

Such an electrochemical sensor is mounted, for example, in an alarm apparatus or the like demanding high reliability, and it thus of great necessity that concentration detection always functions correctly. Specifically, it would be desirable to diagnose whether or not concentration detection in an electrochemical sensor is functioning correctly, and to continue to use the electrochemical sensor when it is functioning correctly and immediately stop use and initiate a replacement procedure when it is not functioning correctly or there is a warning sign that not functioning correctly is imminent.

Patent Literature 1 and 2 have disclosed such a diagnostic method and a diagnostic apparatus for diagnosing an electrochemical sensor.

Patent Literature 1 provides a method for applying a pulse voltage between the sensing electrode and the opposite electrode of an electrochemical sensor, and diagnosing whether or not the electrochemical sensor is accurate on the basis of an output of the electrochemical sensor after the pulse stops; namely, the capacitance output (discharge characteristic). Specifically, it is held that an error such as the electrochemical sensor malfunctioning can be diagnosed by comparing the capacitance output when functioning correctly to the actual measured capacitance output.

Patent Literature 2 provides a method for diagnosing that an error such as a short between the sensing electrode and the opposite electrode of an electrochemical sensor or a reduction in sensor sensitivity has occurred on the basis of whether the output of the electrochemical sensor is a peak output or a bottom output when turned on again after turning off the power source of a gas detector incorporating the electrochemical sensor.

[Patent Document 1] JP (Kokai) 2000-146908
[Patent Document 2] JP (Kokai) 2004-279293

SUMMARY OF THE INVENTION

The electrochemical sensor described earlier is configured to detect the concentration of a gas to be detected in accordance with an output of a current generated by the sensing electrode oxidizing the gas to be detected. Therefore, the electrolyte solution or solid electrolyte must contain enough moisture for a current to flow between the sensing electrode and the opposite electrode via the electrolyte solution or solid electrolyte. In the event that the electrolyte solution or solid electrolyte becomes dry, the output of current by the electrochemical sensor fluctuates, producing a state in which the sensor cannot accurately detect the concentration of the gas to be detected in the atmosphere. Specifically, when the electrolyte solution or solid electrolyte becomes dry, the output of current by the electrochemical sensor decreases irrespective of the concentration of the gas to be detected, producing a problem in that the sensor cannot accurately detect the concentration of the gas to be detected.

The electrochemical sensor diagnostic method and diagnostic apparatus of Patent Literature 1 and 2 can diagnose that the electrolyte solution or solid electrolyte has become completely dry and a current is no longer flowing between the sensing electrode and the opposite electrode, causing an insulated state in which the reaction to the gas is lost and an error starts to occur. Merely diagnosing that an error has started to occur when moisture has completely dried, however, risks creating a period during which the gas to be detected cannot be accurately detected and high reliability cannot be ensured in a case such as when the electrochemical sensor is used, for example, in an alarm device or the like that demands high reliability.

Therefore, an object of the present invention, which was devised with the foregoing aspects of the prior art in view, is to establish an electrochemical sensor diagnostic method and an electrochemical sensor diagnostic apparatus capable of straightforwardly and reliably making a diagnosis by identifying a warning sign stage (an early stage before an error appears in the sensor output), as an "error state". The warning sign stage is a stage deviating from a "normal state" in which there is enough moisture in the electrolyte solution or solid electrolyte, and in the warning sign stage, the output of the electrochemical sensor for detecting the concentration of a gas to be detected will be lost.

The invention is a method for diagnosing an electrochemical sensor comprising a sensor unit including a solid or liquid electrolyte between a sensing electrode with which a gas to be detected makes contact and an opposite electrode, wherein the concentration of the gas to be detected is detected on the basis of a current flowing between the sensing electrode and the opposite electrode, or a voltage corresponding to the current, and a characteristic means is connecting a water tank to a lower part of the sensor unit for accommodating water or an absorbent polymer that has been caused to absorb water in an inner space thereof, the water present in the inner space being supplied to the electrolyte in the sensor unit, and diagnosing whether or not the electrochemical sensor is in an error state representing a process of moving from a desiccated state in which there is no water at all in the water tank and there is not enough moisture in the electrolyte, to a completely dry state in which there is no moisture at all in the electrolyte when a resistance of the electrolyte is increased.

Since the means according to the present aspect performs a diagnosis on the basis of an increase in the resistance of the electrolyte, it can straightforwardly and reliably diagnose an electrochemical sensor by taking a warning sign stage (an early stage before an error appears in the sensor output), to be an "error state". The warning sign stage is a stage deviating from a "normal state" in which there is enough moisture in the electrolyte solution or solid electrolyte, and in the warning sign stage, the output of the electrochemical sensor for detecting the concentration of a gas to be detected will be lost.

Specifically, the resistance in an electrolyte increases during the process of moving from a "normal state" (moist state) in which there is enough moisture in the electrolyte disposed between a sensing electrode for contacting a gas to be detected and an opposite electrode, to a state in which the moisture has completely dried (completely dry state). Therefore, the resistance of the electrolyte can be used to diagnose when the electrolyte is in a state (desiccated state) of being in the process of moving from the moist state to the completely dry state. This desiccated state is a state in which there is not enough moisture in the electrolyte, and is an "error state" in which the output of the electrochemical sensor is nearly normal, but the resistance in the electrolyte has risen. The state in which the electrolyte is completely free of moisture (completely dry state) is a state in which the output of the electrochemical sensor has ceased.

Therefore, the means according to the present aspect can straightforwardly and reliably diagnose whether or not the sensor is in an error state in which there is not enough moisture or no moisture at all in the electrolyte (desiccated state or completely dry state) and the resistance in the electrolyte of the electrochemical sensor has increased.

Hence, it can be ascertained that the moisture in an electrolyte is about to disappear at a stage (desiccated state) before the moisture in the electrolyte completely dries and the output of a sensor drops, and a countermeasure, such as replacing the electrochemical sensor, can be adopted before the function of the electrochemical sensor for detecting the concentration of a gas to be detected, for example, starts to drop.

In a preferred aspect of the method for diagnosing an electrochemical sensor according to the present invention comprising, the resistance of the electrolyte being an impedance of the electrochemical sensor in a state in which an alternating current or an alternating voltage has been applied in the electrochemical sensor; and making a diagnosis that the electrochemical sensor is in the error state when there has been found an increase in impedance relative to the normal impedance, which is the impedance of the electrochemical sensor in a normal state. Alternating current refers to a current that is not a direct current and in which the current varies cyclically over time, such as an alternating current or a pulse rectangular current. In the description hereinafter, alternating current will refer to a similar current. Alternating voltage refers to a voltage that is not a direct voltage, and in which voltage varies cyclically over time, such as an alternating voltage or a pulse rectangular voltage. In the description hereinafter, alternating voltage will refer to a similar voltage. The normal state of an electrochemical sensor is a state in which there is enough moisture in the electrolyte, as described earlier.

The means according to the present aspect diagnose that an electrochemical sensor is in an error state when a resistance component (impedance) matching an electrolyte in an equivalent circuit corresponding to the electrochemical sensor shows an increase in impedance relative to the normal impedance in the normal state (moist state) described earlier. Therefore, the means according to the present aspect can more reliably diagnose in advance a state in which the output of the electrochemical sensor will be affected at a stage (desiccated state) before the moisture in the electrolyte completely dries.

Specifically, the resistance component (impedance) matching an electrolyte in an equivalent circuit corresponding to the electrochemical sensor can be obtained in a state in which the reaction (polarization) resistance component (impedance) at the sensing electrode and the opposite electrode in this equivalent circuit can be virtually ignored by applying an alternating current or an alternating voltage to the electrochemical sensor, and can be fetched as an indicator that more accurately reflects the resistance component (impedance) of the electrolyte. A reduction in conductivity in the electrolyte when there is not enough or no moisture at all in the electrolyte (desiccated state or completely dry state) causes the resistance component (impedance) of the electrolyte to increase. Therefore, an error state in which the resistance in the electrolyte is rising can be diagnosed more accurately and reliably when this impedance has increased relative to the normal impedance in the normal state.

Hence, it can be known more accurately that the moisture in an electrolyte is starting to decrease at a stage (desiccated state) before the moisture in the electrolyte completely dries.

In a preferred aspect of the method for diagnosing an electrochemical sensor according to the present invention comprising, calculating the impedance using an output voltage or an output current of the electrochemical sensor in a state where an alternating current has been applied in the electrochemical sensor; and making a diagnosis that the electrochemical sensor is in the error state in which there has been found an increase of impedance, when there has been found an increase of voltage relative to the normal voltage, which is the output voltage of the electrochemical sensor in the normal state, or when there has been found a decrease in current relative to the normal current, which is the output current of the electrochemical sensor in the normal state. As described earlier, the normal state of the electrochemical sensor is the state in which there is enough moisture in the electrolyte.

The means according to the present aspect diagnoses that an electrochemical sensor is in an error state when the output voltage of the electrochemical sensor during a flow of alternating current increases relative to the normal voltage in the normal state (moist state) described earlier. Therefore, the means according to the present aspect can more reliably diagnose in advance a state in which the output of the electrochemical sensor will be affected at a stage (desiccated state) before the moisture in the electrolyte completely dries.

Specifically, the resistance component (impedance) matching an electrolyte in an equivalent circuit corresponding to the electrochemical sensor is placed in a state in which the reaction resistance component (impedance) at the sensing electrode and the opposite electrode in this equivalent circuit can be virtually ignored by applying an alternating current to the electrochemical sensor, and is an indicator that more accurately reflects the resistance component (impedance) of the electrolyte, but the output voltage corresponding to this resistance component (impedance) is an indicator that more accurately reflects the resistance component (impedance) of the electrolyte. A reduction in conductivity in the electrolyte when there is not enough or no moisture at all in the electrolyte (desiccated state or completely dry state) causes the output voltage of the electrolyte to increase when an alternating current is applied. Therefore, an error state can be diagnosed more accurately and reliably when the output voltage of the electrolyte is increasing relative to the normal voltage in the normal state. When using the output current instead of the output voltage, the electrochemical sensor can be diagnosed to be in an error state when a decrease in current is found relative to the normal current, which is the output current of the electrochemical sensor in the normal state.

In a preferred aspect of the method for diagnosing an electrochemical sensor according to the present invention, an alternating current having a frequency of 10 Hz or greater is applied as the alternating current.

The means according to the present aspect can more accurately and reliably diagnose that an electrochemical sensor is in an error state by virtually ignoring the reaction resistance component (impedance) at the sensing electrode and the opposite electrode among the electrical characteristics of the electrochemical sensor because an alternating current having a frequency of 10 Hz or greater flows in the electrochemical sensor, and using the stabilized impedance of the electrolyte or the output voltage corresponding to this impedance. The upper limit of the frequency is not particularly limited, but is about 10,000 Hz.

In a preferred aspect of the method for diagnosing an electrochemical sensor according to the present invention comprising, calculating the impedance using an output current or an output voltage of the electrochemical sensor in a state where an alternating voltage is applied to the electrochemical sensor; and making a diagnosis that the electrochemical sensor is in the error state in which there has been found an increase of impedance, when there has been found a decrease in current relative to the normal current, which is the output current of the electrochemical sensor in the normal state, or there has been found an increase of voltage relative to the normal voltage, which is the output voltage of the electrochemical sensor in the normal state. As described earlier, the normal state of the electrochemical sensor is the state in which there is enough moisture in the electrolyte.

According to the means of the present aspect, as when applying an alternating current to an electrochemical sensor as described earlier, applying an alternating voltage to an electrochemical sensor produces a state in which the reaction resistance component (impedance) at the sensing electrode and the opposite electrode in the equivalent circuit can be virtually ignored, and this is an indicator that more accurately reflects the resistance component (impedance) of the electrolyte, but the output current corresponding to this resistance component (impedance) is also an indicator that more accurately reflects the resistance component (impedance) of the electrolyte. A reduction in conductivity in the electrolyte when there is not enough or no moisture at all in the electrolyte (desiccated state or completely dry state) causes the output current of the electrolyte to decrease when an alternating voltage is applied. Therefore, an error state can be diagnosed more accurately and reliably when the output current of the electrolyte decreases relative to the normal current in the normal state. When using the output voltage instead of the output current, the electrochemical sensor can be diagnosed to be in an error state when an increase in voltage is found relative to the normal voltage, which is the output voltage of the electrochemical sensor in the normal state.

In a preferred aspect of the method for diagnosing an electrochemical sensor according to the present invention, an alternating voltage having a frequency of 10 Hz or greater is applied as the alternating voltage.

The means according to the present aspect can more accurately and reliably diagnose that an electrochemical sensor is in an error state by virtually ignoring the reaction resistance component (impedance) at the sensing electrode and the opposite electrode among the electrical characteristics of the electrochemical sensor because an alternating voltage having a frequency of 10 Hz or greater is applied to the electrochemical sensor, and using the stabilized impedance of the electrolyte or the output current corresponding to this impedance. The upper limit of the frequency is not particularly limited, but is about 10,000 Hz.

The invention is an apparatus for diagnosing an electrochemical sensor comprising a sensor unit including a solid or liquid electrolyte between a sensing electrode with which a gas to be detected makes contact and an opposite electrode, wherein the concentration of the gas to be detected is detected on the basis of a current flowing between the sensing electrode and the opposite electrode, or a voltage corresponding to the current, and wherein a water tank is connected to a lower part of the sensor unit for accommodating water or an absorbent polymer that has been caused to absorb water in an inner space thereof, the water present in the inner space being supplied to the electrolyte in the sensor unit, the apparatus comprising, detecting means for detecting a resistance of the electrolyte; and diagnosing means for diagnosing whether or not the electrochemical sensor is in an error state representing a process of moving from a desiccated state in which there is no water at all in the water tank and there is not enough moisture in the electrolyte, to a completely dry state in which there is no moisture at all in the electrolyte when the resistance of the electrolyte detected by the detecting means is increased. The apparatus is configured to perform the method for diagnosing the electrochemical sensor as described above.

According to the electrochemical sensor diagnostic apparatus of the present aspect, the detecting means detects the resistance of the electrolyte, and the diagnosing means makes a diagnosis, on the basis of the resistance of the electrolyte in the electrochemical sensor, as to whether the electrochemical sensor is in an error state where there has been an increase in the resistance of the electrolyte in the sensor. So it can straightforwardly and reliably diagnose whether or not the electrochemical sensor is in an error state.

Specifically, the resistance in the electrolyte increases during the process of moving from a normal state (moist state) in which there is enough moisture in the electrolyte disposed between the sensing electrode for detecting a gas to be detected and the opposite electrode to a state in which this moisture has completely dried (completely dry state). Therefore, it is possible to use the resistance of the electrolyte to diagnose the presence of a state (desiccated state) where the electrolyte is in the process of moving from the moist state to the completely dry state. The desiccated state is a state in which there is not enough moisture in the electrolyte, and is an "error state" in which the output of the electrochemical sensor is nearly normal, but the resistance in the electrolyte has risen. The state in which the moisture in the electrolyte has completely dried (completely dry state) is a state in which the output of the electrochemical sensor has ceased.

Therefore, the apparatus according to the present aspect can straightforwardly and reliably diagnose whether the sensor is in an error state in which there is not enough moisture or no moisture at all in the electrolyte (desiccated state or completely dry state) and the resistance in the electrolyte of the electrochemical sensor is rising.

Hence, it can be ascertained that the moisture in an electrolyte is about to disappear at a stage (desiccated state) before the moisture in the electrolyte has completely dried and the output of the sensor has dropped, and a countermeasure, such as replacing the electrochemical sensor, can be adopted before the function of an electrochemical sensor for detecting the concentration of a gas to be detected, for example, starts to drop.

In a preferred aspect of the apparatus for diagnosing an electrochemical sensor according to the present invention, the resistance of the electrolyte is an impedance of the electrochemical sensor in a state where an alternating current or an alternating voltage has been applied in the electrochemical sensor; and the diagnosing means makes a diagnosis that the electrochemical sensor is in the error state when there has been found an increase of impedance relative to the normal impedance, which is the impedance of the electrochemical sensor in the normal state. The normal state of an electrochemical sensor is a state in which there is enough moisture in the electrolyte as described earlier.

According to this aspect, the diagnosing means makes a diagnosis that an electrochemical sensor is in an error state when a resistance component (impedance) matching an electrolyte in an equivalent circuit corresponding to the electrochemical sensor shows an increase in impedance relative to the normal impedance in the normal state (moist state) described earlier. Therefore, the apparatus according to the present aspect can more reliably diagnose in advance a state in which the output of the electrochemical sensor will be affected at a stage (desiccated state) before the moisture in the electrolyte completely dries.

Specifically, the resistance component (impedance) matching an electrolyte in an equivalent circuit corresponding to the electrochemical sensor can be obtained in a state in which the reaction resistance component (impedance) at the sensing electrode and the opposite electrode in this equivalent circuit can be virtually ignored by applying an alternating current or an alternating voltage to the electrochemical sensor, and can be acquired as an indicator that more accurately reflects the resistance component (impedance) of the electrolyte. A reduction in conductivity in the electrolyte when there is not enough or no moisture at all in the electrolyte (desiccated state or completely dry state) causes the resistance component (impedance) of the electrolyte to increase. Therefore, an error state in which the resistance in the electrolyte is rising can be diagnosed more accurately and reliably when the impedance has increased relative to the normal impedance in the normal state.

Hence, it can be known more accurately that the moisture in an electrolyte is starting to decrease at a stage (desiccated state) before the moisture in the electrolyte completely dries.

In a preferred aspect of the apparatus for diagnosing an electrochemical sensor according to the present invention, the impedance is calculated using an output voltage or an output current of the electrochemical sensor in a state where an alternating current has been applied in the electrochemical sensor; and the diagnosing means makes a diagnosis that the electrochemical sensor is in the error state in which there has been found an increase of impedance, when there has been found an increase of voltage relative to the normal voltage, which is the output voltage of the electrochemical sensor in the normal state, or there has been found a decrease in current relative to the normal current, which is the output current of the electrochemical sensor in the normal state. As described earlier, the normal state of the electrochemical sensor is the state in which there is enough moisture in the electrolyte.

According to this aspect, the diagnosing means makes a diagnosis that an electrochemical sensor is in an error state when the output voltage of the electrochemical sensor during a flow of alternating current increases relative to the normal voltage in the normal state (moist state) described earlier. Therefore, the apparatus according to the present aspect can more reliably diagnose in advance a state in which the output of the electrochemical sensor will be affected at a stage (desiccated state) before the moisture in the electrolyte completely dries.

Specifically, the resistance component (impedance) matching an electrolyte in an equivalent circuit corresponding to the electrochemical sensor is placed in a state in which the reaction resistance component (impedance) at the sensing electrode and the opposite electrode in this equivalent circuit can be virtually ignored by applying an alternating current to the electrochemical sensor, and is an indicator that more accurately reflects the resistance component (impedance) of the electrolyte, but the output voltage corresponding to this resistance component (impedance) is also an indicator that more accurately reflects the resistance component (impedance) of the electrolyte. A reduction in conductivity in the electrolyte when there is not enough or no moisture at all in the electrolyte (desiccated state or completely dry state) causes the output voltage of the electrolyte to increase when an alternating current is applied. Therefore, an error state can be diagnosed more accurately and reliably when the output voltage of the electrolyte is increasing relative to the normal voltage in the normal state. When using the output current instead of the output voltage, the electrochemical sensor can be diagnosed to be in an error state when a decrease in current is found relative to the normal current, which is the output current of the electrochemical sensor in the normal state.

In a preferred aspect of the apparatus for diagnosing an electrochemical sensor according to the present invention, the impedance is calculated using an output current or an output voltage of the electrochemical sensor in a state where an alternating voltage is applied to the electrochemical sensor; and the diagnosing means makes a diagnosis that the electrochemical sensor is in the error state in which there has been found an increase of impedance, when there has been found a decrease in current relative to the normal current, which is the output current of the electrochemical sensor in the normal state, or there has been found an increase of voltage relative to the normal voltage, which is the output voltage of the electrochemical sensor in the normal state. As described earlier, the normal state of the electrochemical sensor is the state in which there is enough moisture in the electrolyte.

According to this aspect, as when applying an alternating current to an electrochemical sensor as described earlier, applying an alternating voltage to an electrochemical sensor produces a state in which the reaction resistance component (impedance) at the sensing electrode and the opposite electrode in the equivalent circuit can be virtually ignored, and this is an indicator that more accurately reflects the resistance component (impedance) of the electrolyte, but the output current corresponding to this resistance component (impedance) is also an indicator that more accurately reflects the resistance component (impedance) of the electrolyte. A reduction in conductivity in the electrolyte when there is not enough or no moisture at all in the electrolyte (desiccated state or completely dry state) causes the output current of the electrolyte to decrease when an alternating voltage is applied. Therefore, an error state can be diagnosed more accurately and reliably when the output current of the electrolyte is decreasing relative to the normal current in the normal state. When using the output voltage instead of the output current, the electrochemical sensor can be diagnosed to be in an error state when an increase in voltage is found relative to the normal voltage, which is the output voltage of the electrochemical sensor in the normal state.

DESCRIPTION OF THE PREFERRED EMBODIMENTS

Figure 1:
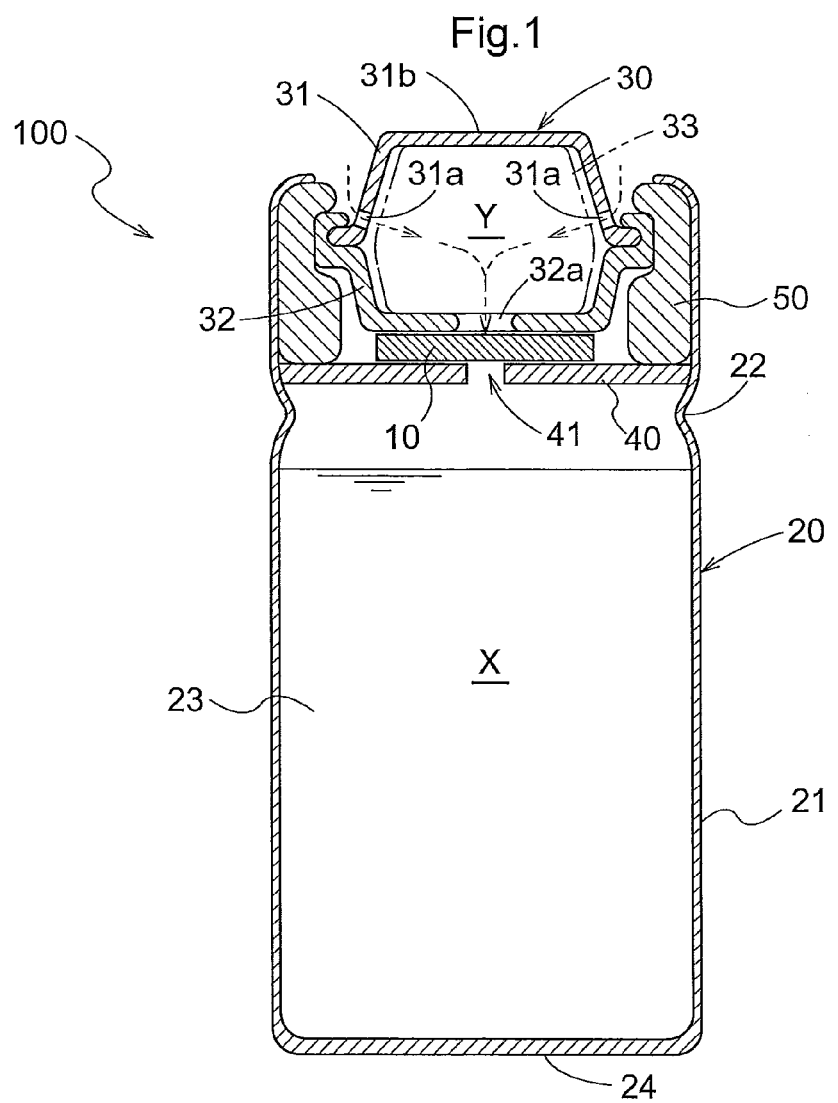
FIG. 1 is a vertical cross-sectional view showing the overall configuration of an electrochemical sensor.

Embodiments of the present invention will be described hereinafter with reference to the annexed drawings. The present invention is not limited to the embodiments or the configurations illustrated in the drawings; various variations and modifications may be made.

Basic Structure of Electrochemical Sensor

Figure 2:
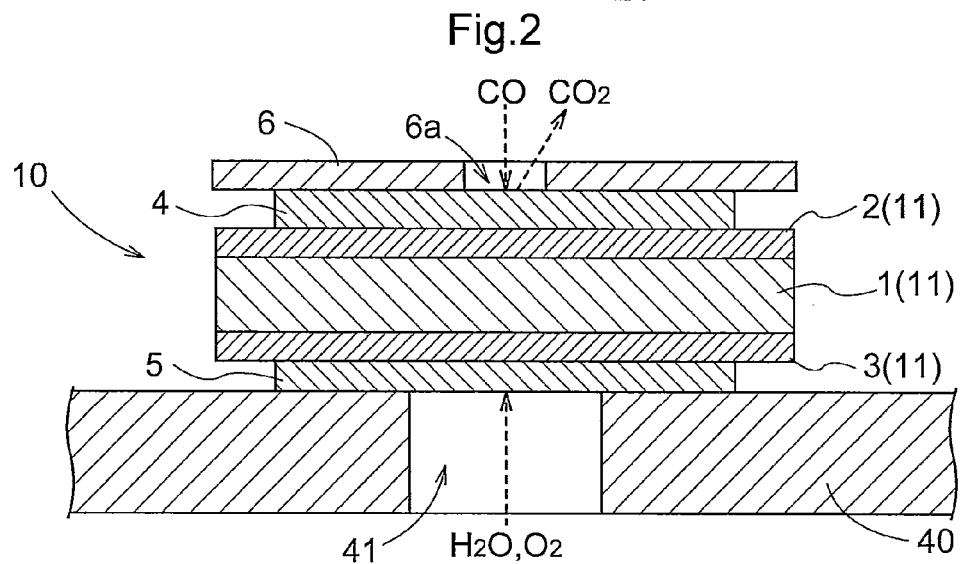
FIG. 2 is a vertical cross-sectional view of a sensor unit that is an essential component of an electrochemical sensor.

FIG. 1 is a vertical section view showing the overall configuration of an electrochemical sensor 100 used in the electrochemical sensor diagnostic method and diagnostic apparatus of the present invention. FIG. 2 is a vertical section view of a sensor unit 10 that is an essential component of the electrochemical sensor 100.

The electrochemical sensor 100 of this embodiment is a CO sensor for which the gas to be detected is carbon monoxide. The basic structure has the sensor unit 10, a water tank 20, a filter section 30, a washer 40, a gasket 50, and the like.

As shown in FIG. 2, the sensor unit 10 has sensor means 11 having a laminate structure in which an anode 2 is connected as a sensing electrode and a cathode 3 is connected as an opposite electrode to the two sides (top and bottom) of an electrolyte layer 1, conductive hydrophobic films 4, 5 to be described later, and a diffusion control plate 6.

As will be described later, the electrolyte layer 1 functions as a medium when cations such as protons ($H^+$) generated during oxidation of carbon monoxide at the anode 2 migrate to the cathode 3 (or anions such as $OH^-$ migrate from the cathode 3 to the anode 2), and may comprise a substrate such as a filter paper impregnated with an electrolyte solution containing an aromatic sulfonate (polymer) represented by the following chemical formula.

[Chemical 1]

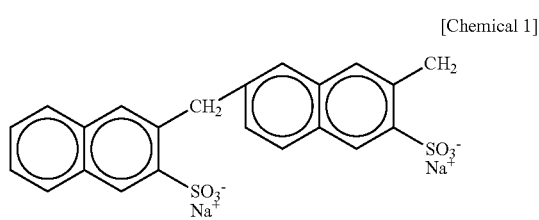

A reference electrode (not shown) may be interposed in the electrolyte layer 1. In this case, the electrolyte layer 1 is divided into two upper and lower layers, and the reference electrode is placed between the two layers.

The anode 2 is an electrode catalyst for oxidizing carbon monoxide to carbon dioxide, for which a platinum catalyst or the like is usually used. The cathode 3 has substantially the same configuration as the anode 2. In this embodiment, the thickness of each of the anode 2 and the cathode 3 is set at about 0.05 to 0.2 mm.

The conductive hydrophobic films 4, 5 are disposed above the anode 2 and below the cathode 3, respectively. These conductive hydrophobic films 4, 5 comprise gas-permeable membranes that are permeable by the gases (carbon monoxide, carbon dioxide, water vapor, and oxygen) involved in a reaction at the anode 2 or the cathode 3.

The diffusion control plate 6 is disposed above the conductive hydrophobic film 4 above the anode 2. This diffusion control plate 6 controls the flow of outside air such that carbon monoxide gas containing outside air contacts the anode 2 by controlled diffusion. Specifically, a diffusion control hole 6a is formed in the diffusion control plate 6, and the supply of outside air and CO molecules supplied to the anode 2 is controlled through this diffusion control hole 6a. Therefore, in the event that the concentration of carbon monoxide contained in the outside air is high and the carbon monoxide is conducted to the anode 2 without modification, the action of the diffusion control hole 6a disposed in the diffusion control plate 6 can completely oxidize all of the CO at the anode 2 even when oxidation at the anode 2 cannot keep up due to excess carbon monoxide.

In this embodiment, the diffusion control plate 6 is formed of a thin plate comprising a metal such as stainless steel, and the diffusion control hole 6a is formed by any desired method, such as punching.

The water tank 20 is connected to the sensor unit 10 below the cathode 3. The water tank 20 has a constricted section 22 formed in part of its outer wall 21, and the washer 40, which is formed with a hole 41 in the center, is held in place by this constricted section 22. Water or an absorbent polymer 23 that has been caused to absorb water is accommodated in the space X enclosed by the outer wall 21 and the washer 40. The water in the space X passes through the hole 41 in the washer 40 in the form of water vapor, and is supplied to the electrolyte layer 1 through the cathode 3 of the sensor unit 10.

The filter section 30 is disposed on the sensor unit 10 above the anode 2. The filter section 30 comprises a lower half section 32, in which a second through hole 32a has been formed, crimped to an upper half section 31, in which a first through hole 31a has been formed, to form a hollow section Y; and this hollow section Y filled with an activated carbon filter 33. In this configuration, carbon monoxide contained in the outside air infiltrates from the first through hole 31a, and is supplied from the second through hole 32a to the anode 2 of the sensor unit 10 after impurities and the like are removed by the activated carbon filter 33.

A gasket 50 is disposed between the filter section 30 and the outer wall 21 of the water tank 20 to prevent evaporating water escaping from the water tank 20.

The floor face 24 of the water tank 20 and the top face 31b of the upper half section 31 function as electrode terminals in the electrochemical sensor 100 of this embodiment. Therefore, the upper half section 31 and the lower half section 32 of the filter section 30, the diffusion control plate 6 of the sensor unit 10, the washer 40, and the outer wall 21 of the water tank 20 are made of a conductive material such as metal.

Figure 3:
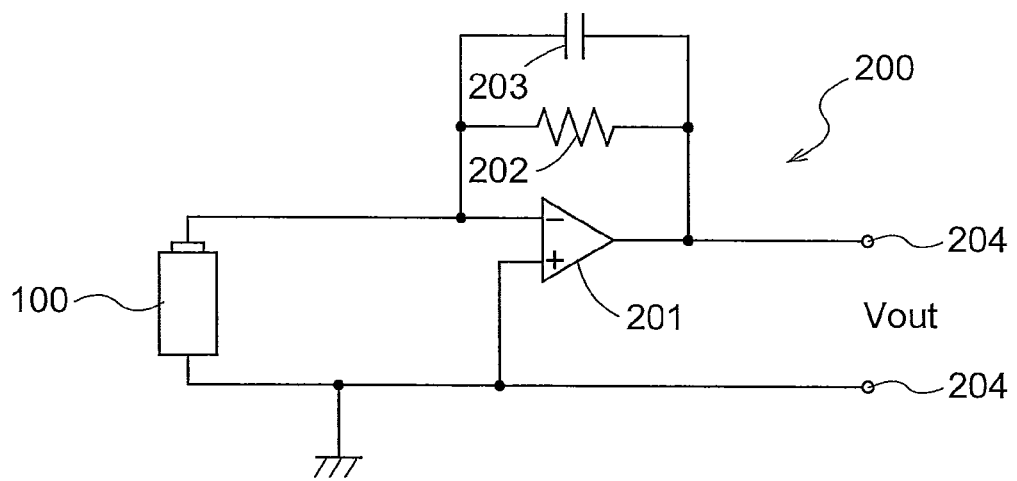
FIG. 3 is a basic measurement circuit diagram of a bipolar electrochemical sensor.

The electrochemical sensor 100 so configured has a basic measurement circuit 200 such as shown, for example, by FIG. 3. This basic measurement circuit 200 is used for the measurement method when the electrochemical sensor 100 is a bipolar model.

A minute current (short-circuit current) generated by the sensor unit 10 of the electrochemical sensor 100 is amplified and converted by an operational amplifier 201, a resistor 202, and a capacitor 203, and outputted from an output terminal 204 as voltage $V_{out}$ (electrochemical sensor output). Next, the concentration of carbon monoxide contained in the outside air is detected in the electrochemical sensor 100, based on the output results. The short-circuit current flows from the anode 2 to the cathode 3 through the electrolyte, and from the cathode 3 to the anode 2 through an external circuit.

Detection of Concentration by Electrochemical Sensor

When carbon monoxide contacts the anode 2 (sensing electrode) of the electrochemical sensor 100, the carbon monoxide reacts with water at the anode 2 to generate carbon dioxide as well as protons ($H^+$) and electrons ($e^-$) as indicated by the following (1).

$$CO+H_2O \rightarrow CO_2+2H^++2e^- \quad (1)$$

The reaction of (1) is basically a diffusion-controlled reaction which is dependent on the speed at which carbon monoxide diffuses in the measurement atmosphere (diffusion is controlled by oxidation of carbon monoxide near the mixed potential of the anode 2, where both oxygen and carbon monoxide are present).

The protons ($H^+$) generated at the anode 2 pass through the electrolyte layer 1 and migrate to the cathode 3 (opposite electrode). The electrons ($e^-$) generated at the anode 2 pass through the basic measurement circuit 200 and migrate to the cathode 3 (opposite electrode), where they react with the oxygen introduced to the opposite electrode and the water in the electrolyte as indicated by the following (2) to generate hydroxyl ($OH^-$). Because oxygen is also present at the anode 2, usually about half of the carbon monoxide is oxidized by the oxygen at the anode 2, and the remaining half is oxidized by the oxygen at the cathode 3.

$$\tfrac{1}{2}O_2+H_2O+2e^- \rightarrow 2OH^- \quad (2)$$

Thus, the concentration of carbon monoxide in the measurement atmosphere can be measured by detecting an electrical characteristic of the electricity flowing from the anode 2 side to the cathode 3 side associated with this reaction; for example, the level of the short-circuit current. Alternatively, the concentration of carbon monoxide in the measurement atmosphere can be measured by detecting the voltage of the open circuit formed by placing the anode 2 and the cathode 3 in an open circuit state.

Figure 4:
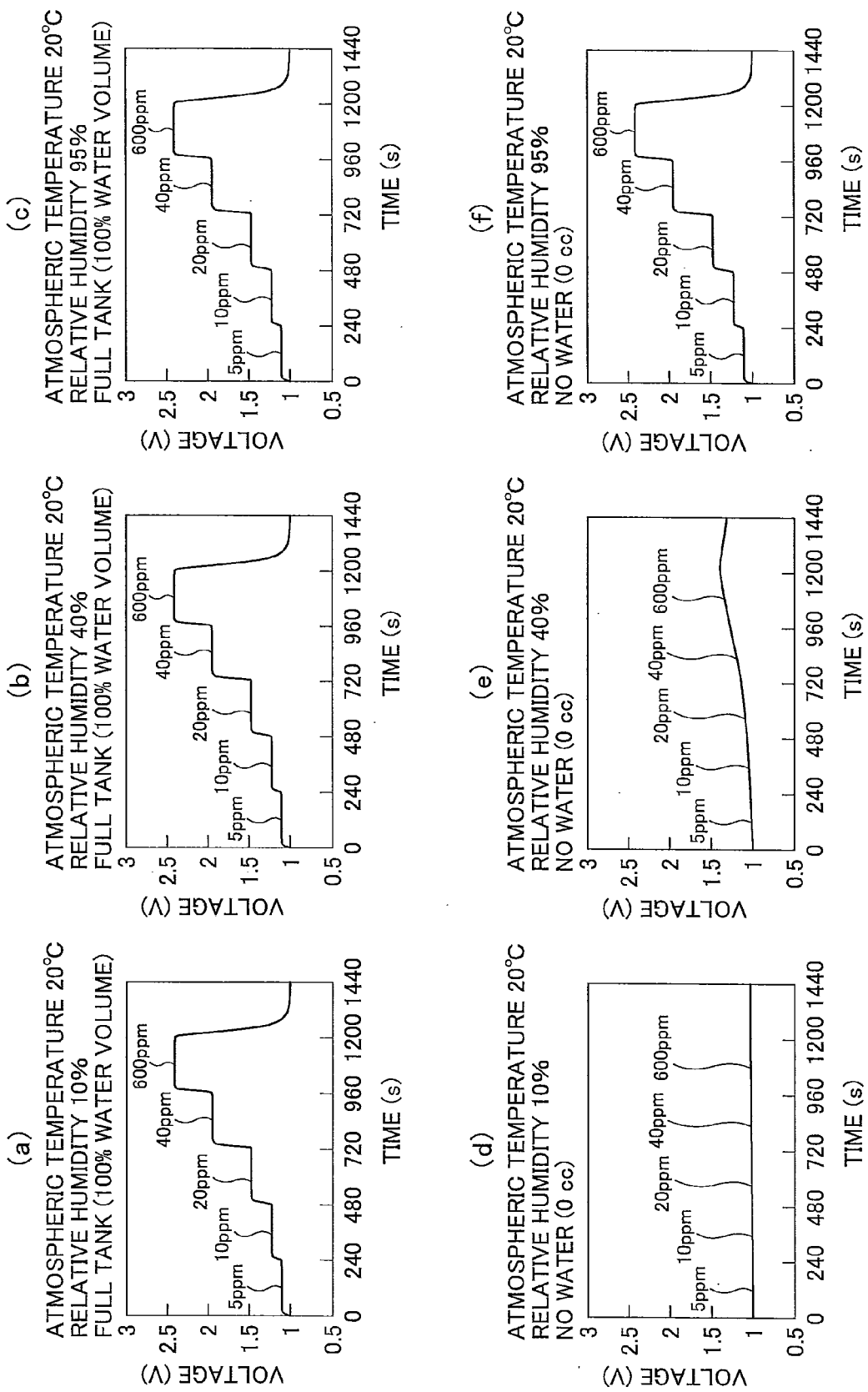
FIG. 4 is a graph showing the relationship between the concentration of carbon monoxide and the output (voltage) of an electrochemical sensor.

Specifically, as shown in FIGS. 4(a), (b), and (c) and 5(a), (b), and (c), the concentration of carbon monoxide in the measurement atmosphere can be measured because the output of the electrochemical sensor 100 (the converted voltage of the short-circuit current flowing in the external circuit from the cathode 3 to the anode 2) shows a specific voltage level depending on the concentration of carbon monoxide in the measurement atmosphere.

FIGS. 4(a), (b), and (c) and 5(a), (b), and (c) show the output (voltage) of the electrochemical sensor 100 when the concentration of carbon monoxide in the atmosphere is converted every 240 seconds with the water in the water tank 20 at a full tank level (100% water volume). FIGS. 4(a), (b), and (c) show the results when the atmosphere temperature is 20° C. and the relative humidity is changed from 10%, 40%, and 95%, respectively; and FIGS. 5(a), (b), and (c) show the results when the atmosphere temperature is 50° C. and the relative humidity is changed from 5%, 40%, and 95%, respectively. Comparable outputs are obtained when the water in the water tank 20 is 20% or less of a full tank.

FIGS. 4(a), (b), and (c) and 5(a), (b), and (c) show the output of the electrochemical sensor 100 in a normal state in which there is enough moisture in the electrolyte in the electrolyte layer 1, and show a specific output (voltage) that depends on the concentration of carbon monoxide. The output of the electrochemical sensor 100 does not fluctuate with variation in the relative humidity of the atmosphere. That is, the electrochemical sensor 100 is in a normal state in which there is enough moisture in the electrolyte layer 1 when showing a specific voltage in stages depending on the concentration of carbon monoxide in the measurement atmosphere.

Figure 5:
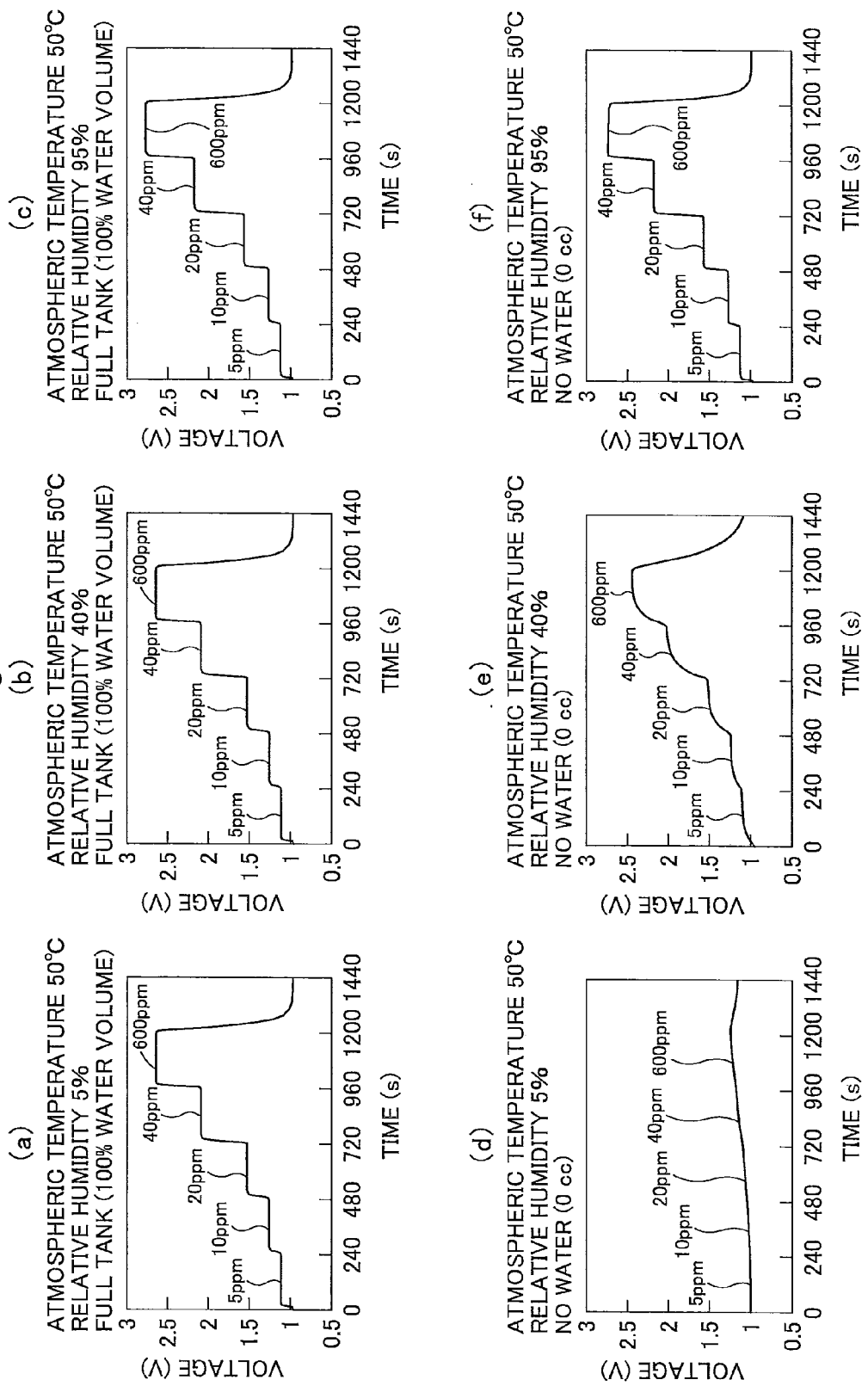
FIG. 5 is a graph showing the relationship between the concentration of carbon monoxide and the output (voltage) of an electrochemical sensor.

As shown in FIGS. 4(d), (e), and (f) and 5(d), (e), and (f), when there is no water at all (0 cc) in the water tank 20 and there is not enough or no moisture at all in the electrolyte in the electrolyte layer 1 (the desiccated state or completely dry state to be described later), the output of the electrochemical sensor 100 is affected by the relative humidity of the atmosphere and fluctuates, the output of the electrochemical sensor 100 no longer shows a specific voltage depending on the concentration of carbon monoxide in the measurement atmosphere, and the concentration of carbon monoxide in the measurement atmosphere cannot be accurately measured. Specifically, when the relative humidity is 95% as shown in FIGS. 4(f) and 5(f), even when there is not enough moisture in the electrolyte in the electrolyte layer 1, the concentration of carbon monoxide can be detected from the output (voltage) of the electrochemical sensor 100 in nearly the same manner as in the normal state because of the effect of moisture in the atmosphere. As the relative humidity drops to 40% and 10%, however, the output (voltage) drops and no longer accurately shows the concentration of carbon monoxide in the atmosphere.

As shown in FIGS. 4(f) and 5(f), even if the output of the electrochemical sensor 100 detects the concentration of carbon monoxide in the atmosphere, all states in which there is no water and the concentration cannot be detected are error states. Specifically, the moist state in which there is enough moisture in the electrolyte is the normal state, the process of moving from this moist state to a completely dry state is the desiccated state, and the state in which the moisture has completely dried is the completely dry state. The object of diagnosis as an error state by the method for diagnosing an electrochemical sensor 100 (described later) is not just the completely dry state, but also the desiccated state.

FIGS. 4(d), (e), and (f) and 5(d), (e), and (f) show the output (voltage) of the electrochemical sensor 100 when the concentration of carbon monoxide in the atmosphere is converted every 240 seconds with no water at all (0 cc) in the water tank 20. FIGS. 4(d), (e), and (f) show the results obtained at an atmosphere temperature 20° C. when the relative humidity was changed from 10%, 40%, and 95%, respectively; and FIGS. 5(d), (e), and (f) show the results obtained at an atmosphere temperature of 50° C. when the relative humidity was changed from 5%, 40%, and 95%, respectively.

Method and Apparatus for Diagnosing Electrochemical Sensor

As described earlier, to accurately detect the concentration of a gas to be detected, it is important that the electrochemical sensor 100 having the electrolyte layer 1 be in a state in which there is enough moisture in the electrolyte layer 1. In other words, it is important to diagnose whether or not the sensor is in a state in which there is not enough moisture in the electrolyte and a state in which the resistance in the electrolyte has increased (desiccated state or completely dry state), and thus perceive an error state as early as possible. Therefore, in the present application, whether or not the sensor is in a state in which the resistance in the electrolyte of the electrochemical sensor 100 has increased (error state) is diagnosed to perceive as early as possible that a state in which the concentration of the gas to be detected cannot be accurately detected is imminent. The diagnosis method and a diagnostic apparatus 300 for the electrochemical sensor 100 will be described hereinafter. The diagnostic apparatus 300 for the electrochemical sensor 100 is configured to include detecting means (in the second embodiment to be described later, the detecting means corresponds to first voltage detecting means 304 in FIG. 8) for detecting an electrical characteristic of the electrolyte layer 1 and comprising a measuring instrument configured capable of detecting at least an electrical characteristic (impedance and/or output voltage), and diagnosing means comprising a computer including a CPU, memory means, and the like (in the second embodiment to be described later, the diagnosing means correspond to diagnosing means 306 in FIG. 8).

First Embodiment

Figure 6:
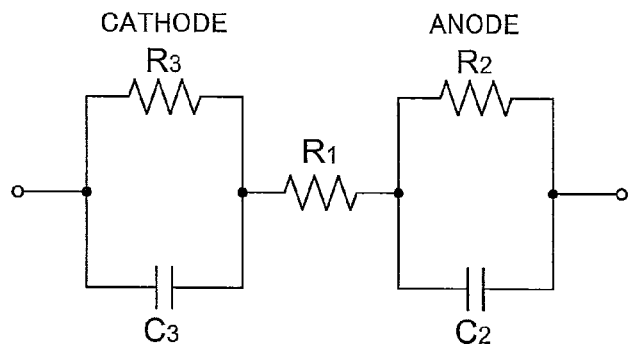
FIG. 6 is a view showing an equivalent circuit of an electrochemical sensor (sensor means)

The sensor means 11 in the sensor unit 10 of the electrochemical sensor 100 is formed by connecting the anode 2 and the cathode 3 to the two sides (top and bottom) of the electrolyte layer 1 as shown in FIG. 2, but the sensor means 11 can be considered as corresponding to an equivalent circuit such as shown in FIG. 6. Specifically, the anode 2 is equivalent to a parallel connected configuration of a reaction resistor $R_2$ and a capacitor (electric double layer capacitor) $C_2$, the cathode 3 is equivalent to a parallel connected configuration of a reaction resistor $R_3$ and a capacitor (electric double layer capacitor) $C_3$, and the electrolyte layer 1 is equivalent to a resistor $R_1$. Therefore, the sensor means 11 corresponds to an equivalent circuit in which the parallel connected configuration of the anode 2 is connected in series to the parallel connected configuration of the cathode 3 with the resistor $R_1$, which is the electrolyte layer 1, in between.

By having an alternating current set, for example, to 10 Hz or greater (about 10 Hz to 10,000 Hz) applied as an alternating current in such sensor means 11, the resistance of $C_2$ and $C_3$ approximate 0 and the current flows through $C_2$ and $C_3$. Therefore, the resistance component (impedance) of the reaction resistors $R_2$ and $R_3$ can be virtually ignored to obtain just the impedance, which is the resistance component, of the resistor $R_1$ of the electrolyte layer 1. The impedance of the electrolyte layer 1 is an indicator that accurately shows the level of moisture in the electrolyte layer 1. Hence, whether or not there is enough moisture in the electrolyte layer 1 can be accurately ascertained. Specifically, as will be described later, the diagnosing means 306 can diagnose a state in which there is not enough moisture in the electrolyte layer 1 (desiccated state) when the impedance of the electrolyte layer 1 has increased relative to the normal impedance in the normal state. Naturally, the diagnosing means can also diagnose a state in which there is no moisture at all in the electrolyte layer 1 (completely dry state).

Figure 7:
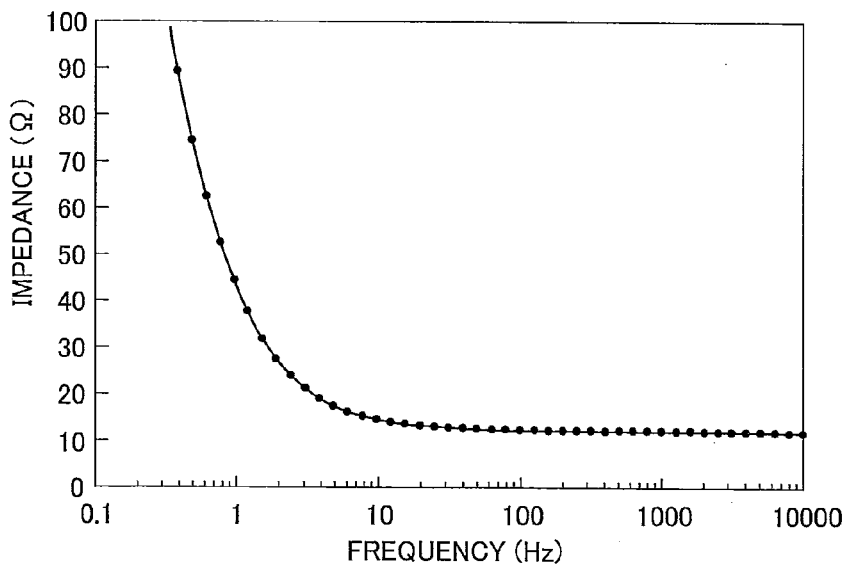
FIG. 7 is a graph showing the relationship between the frequency of an alternating current and the impedance of an electrochemical sensor.

As shown in FIG. 7, the impedance of the electrochemical sensor 100 when an alternating current is flowing in the electrochemical sensor 100 varies depending on the frequency of the alternating current, and the impedance stabilizes near a predetermined level as the frequency becomes higher. Although this stabilized impedance is an indicator that accurately shows the level of moisture in the electrolyte layer 1, when the frequency of the alternating current is, for example, 10 Hz or higher, and preferably 20 Hz or higher, the impedance stabilizes more reliably near the predetermined level, and thus becomes an indicator that more accurately shows the level of moisture in the electrolyte layer 1.

Table 1 show results of having an alternating current impressed in the electrochemical sensor 100 and measuring the impedance of the electrolyte layer 1 using the detecting means.

The impedance is shown when at an atmospheric temperature of 20° C. and a relative humidity of 95%, the water in the water tank 20 is at a full tank level (100% water volume), 20% water volume, or no water (0 cc), and the frequency of the alternating current is 40 Hz or 1 kHz. Table 1 shows impedances measured using three different electrochemical sensors 100 for each water volume.

TABLE 1

|  | Full tank (100% water volume) | 20% Water volume | No water (0 cc) |
|---|---|---|---|
| 1 kHz | 5.35 | 4.89 | 244.64 |
| Impedance | 3.27 | 3.94 | 215.04 |
| [Ω] | 1.29 | 2.65 | 185.64 |
| 40 Hz | 6.73 | 5.40 | 281.61 |
| Impedance | 3.90 | 4.29 | 247.61 |
| [Ω] | 1.63 | 3.09 | 210.61 |

As shown in Table 1, where the impedance of the electrolyte layer 1 shows stationary about the same level of several Ω (normal impedance, which is the diagnosis indicator) when in a normal state in which there is enough moisture in the electrolyte layer 1 (the water in the water tank 20 is a full tank (100% water volume) or 20% water volume (moist state)) while an alternating current is impressed in the sensor means 11 (electrochemical sensor 100) corresponding to the equivalent circuit, the impedance of the electrolyte layer 1 increases greatly to several hundred Ω when there is not enough moisture in the electrolyte layer 1 (when no water is present in the water tank 20 (no water (0 cc)) or the electrolyte layer 1 has at least started to dry (desiccated state)).

Therefore, a state in which there is not enough moisture or no moisture at all in the electrolyte layer 1 can be reliably diagnosed when the impedance of the electrolyte layer 1 has increased relative to the normal impedance in the normal state (several Ω as noted above). Such a diagnosis indicator can be stored in advance in the memory means (not shown) in the diagnosing means 306.

Next, Tables 2 and 3 show results of measuring the impedance of the electrolyte layer 1 using the detecting means and the sensitivity to CO when an alternating current of 1 kHz flowed in the electrochemical sensor 100 and the relative humidity was varied.

This impedance is shown when at atmospheric temperature 20° C. or 50° C., the relative humidity is varied, and the water in the water tank 20 is at a full tank level (100% water volume), 20% water volume, or no water (0 cc). Tables 2 and 3 show impedances measured using four or five different electrochemical sensors 100 for each water volume.

TABLE 2

| | 1 kHz 20° C. | | Full tank (100% water volume) | 20% Water volume | No water (0 cc) |
|---|---|---|---|---|---|
| Low humidity | Impedance [Ω] | | 34.4 | 33.3 | 79998 |
| | | | 32.6 | 37.0 | 82498 |
| | | | 40.5 | 33.9 | 83698 |
| | | | 47.2 | 44.3 | 41898 |
| | | | | 35.2 | 84198 |
| | CO sensitivity | | ○ | ○ | X |
| Moderate humidity | Impedance [Ω] | | 37.4 | 36.2 | 71998 |
| | | | 38.2 | 46.8 | 67998 |
| | | | 19.0 | 39.6 | 69998 |
| | | | 37.7 | 43.7 | 71998 |
| | | | | 50.6 | 30998 |
| | CO sensitivity | | ○ | ○ | X |
| High humidity | Impedance [Ω] | | 13.5 | 14.6 | 8898 |
| | | | 15.4 | 15.4 | 6468 |
| | | | 10.3 | 13.8 | 8468 |
| | | | 18.2 | 15.8 | 8818 |
| | | | | 18.2 | 5188 |

TABLE 2-continued

| | 1 kHz 20° C. | Full tank (100% water volume) | 20% Water volume | No water (0 cc) |
|---|---|---|---|---|
| High humidity (prolonged) | CO sensitivity | ○ | ○ | Δ |
| | Impedance [Ω] | 2.7 | 3.5 | 245 |
| | | 1.3 | 4.9 | 186 |
| | | 3.7 | 2.7 | 232 |
| | | 5.4 | 4.5 | 208 |
| | | | 4.2 | 206 |
| | CO sensitivity | ○ | ○ | ○ |

TABLE 3

| | 1 kHz 50° C. | Full tank (100% water volume) | 20% Water volume | No water (0 cc) |
|---|---|---|---|---|
| Low humidity | Impedance [Ω] | 18.6 | 18.5 | 79998 |
| | | 19.3 | 21.3 | 71398 |
| | | 22.8 | 20.6 | 75898 |
| | | 27.4 | 24.9 | 29498 |
| | | | 20.6 | 79498 |
| | CO sensitivity | ○ | ○ | X |
| Moderate humidity | Impedance [Ω] | 12.2 | 11.8 | 7598 |
| | | 14.1 | 14.0 | 5058 |
| | | 14.7 | 12.7 | 6998 |
| | | 17.8 | 21.5 | 6068 |
| | | | 14.4 | 6528 |
| | CO sensitivity | ○ | ○ | Δ |
| High humidity | Impedance [Ω] | 5.8 | 5.0 | 270 |
| | | 9.1 | 7.0 | 203 |
| | | 8.1 | 8.5 | 270 |
| | | 9.1 | 7.3 | 253 |
| | | | 9.7 | 244 |
| | CO sensitivity | ○ | ○ | ○ |

As shown in Tables 2 and 3, whereas the impedance of the electrolyte layer 1 shows stationary about the same level of several Ω to several tens of Ω (normal impedance, which is the diagnosis indicator) when in a normal state in which there is enough moisture in the electrolyte layer 1 (the water in the water tank 20 is a full tank (100% water volume) or 20% water volume (moist state)) while a 1 kHz alternating current is impressed in the sensor means 11 (electrochemical sensor 100) corresponding to the equivalent circuit, the impedance of the electrolyte layer 1 increases greatly from several hundred Ω to several tens of thousands of Ω when there is not enough moisture in the electrolyte layer 1 (no water in the water tank 20 (0 cc)), the electrolyte layer 1 has at least started to dry (desiccated state), or the electrolyte layer 1 has completely dried (completely dry state).

Therefore, the diagnosing means 306 can reliably diagnose a state in which there is not enough moisture or no moisture at all in the electrolyte layer 1 when the impedance of the electrolyte layer 1 has increased relative to the normal impedance in the normal state (several Ω to several tens of Ω as noted above).

In particular, although sensitivity to CO sometimes appears (indicated by O in the tables) as shown in the 0 cc and high humidity (prolonged) columns of Table 2 and the 0 cc and high humidity columns of Table 3, sensitivity to CO drops at lower humidity (shown by Δ and x in the tables). Specifically, the process of the sensitivity going from O through Δ to x is believed to be the process by which a state (desiccated state) where the electrolyte layer 1 does not have adequate moisture moves to a completely dry state in which there no moisture is present at all, and an error state is presumed to have occurred due to the increased resistance in the electrolyte of the electrochemical sensor 100. As shown by the no water (0 cc) and high humidity (prolonged) columns of Table 2 and the no water (0 cc) and high humidity columns of Table 3, the impedance in the desiccated state (the state in which the sensor output is normal, but complete dryness is imminent) is several hundred Ω (for example, about 200 to 300Ω). Therefore, even though sensitivity to CO may be good despite a state being in effect where there is not enough moisture in the electrolyte layer 1, when the impedance of the electrolyte layer 1 is several hundred Ω (for example, about 200Ω) or more, it can be straightforwardly and reliably diagnosed that the electrolyte layer 1 is in the process (desiccated state) of moving over time to a completely dry state in which the electrolyte layer 1 is completely free of moisture, and an error state due to a rise in the resistance in the electrolyte of the electrochemical sensor 100 is in effect. The reason why CO sensitivity is good even when the resistance of the electrolyte is about 200 to 300Ω is that the total resistance of the sensor, including reaction resistance, is several tens to several hundred kΩ.

Hence, it can be simply and reliably ascertained that the sensor is in a state in which there is not enough moisture in the electrolyte layer 1 (desiccated state) and is in an error state due to a rise in the resistance in the electrolyte of the electrochemical sensor 100; and the electrochemical sensor 100 can be reliably replaced or otherwise attended to before an error is evident in the sensor output.

Second Embodiment

In the first embodiment described earlier, the diagnosing means 306 diagnoses whether or not a sensor is in an error state according to whether or not the impedance of the electrolyte layer 1 increases when an alternating current is applied. When a pulse rectangular voltage is applied instead of an alternating current, however, the output voltage of the electrochemical sensor corresponds to the impedance of the electrochemical sensor. Therefore, whether or not a sensor is in an error state can also be diagnosed by intermittently detecting the impedance of the electrochemical sensor when an alternating current is flowing by detecting the output voltage of the electrochemical sensor when a pulse rectangular voltage is applied.

Figure 8:
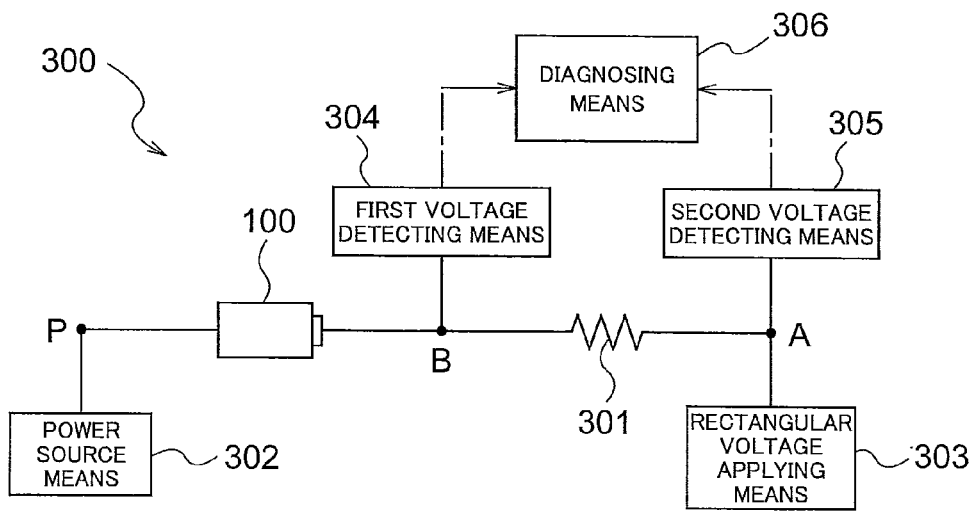
FIG. 8 is a circuit diagram of a diagnostic apparatus including an electrochemical sensor.

A more detailed description now follows. As shown in FIG. 8, the diagnostic apparatus 300 comprises a load resistor 301 (for example, a 1 kΩ load resistor) and an electrochemical sensor 100 connected in series, power source means 302 for applying a constant voltage to a point P upstream of the electrochemical sensor 100, and rectangular voltage applying means 303 for applying a pulse rectangular voltage to a point A directly immediately downstream of the output of the load resistor 301. The diagnostic apparatus 300 also has first voltage detecting means 304 for detecting a point-B voltage at a point B immediately downstream from the electrochemical sensor 100, second voltage detecting means 305 for detecting the point-A voltage at point A immediately downstream from the load resistor 301, and diagnosing means 306 capable of accepting input of the point-B voltage from the first voltage detecting means 304 and the point-A voltage from the second voltage detecting means 305 and diagnosing whether or not the electrochemical sensor 100 is in an error state. The power source means 302 produces 1.0 V as the constant voltage for applying to the point P, and the rectangular voltage applying means 303 produces a pulse rectangular voltage switching between 2.0 V and 0 V as the rectangular voltage for applying to the point A. That is, with point P as a reference, ±1.0 V is applied between P and A to measure the voltage (potential) at point B. The voltage (1.0 V) to be applied to point P and the rectangular voltage (2.0 V and 0 V) to be applied to point A may be suitably modified.

Figure 9:
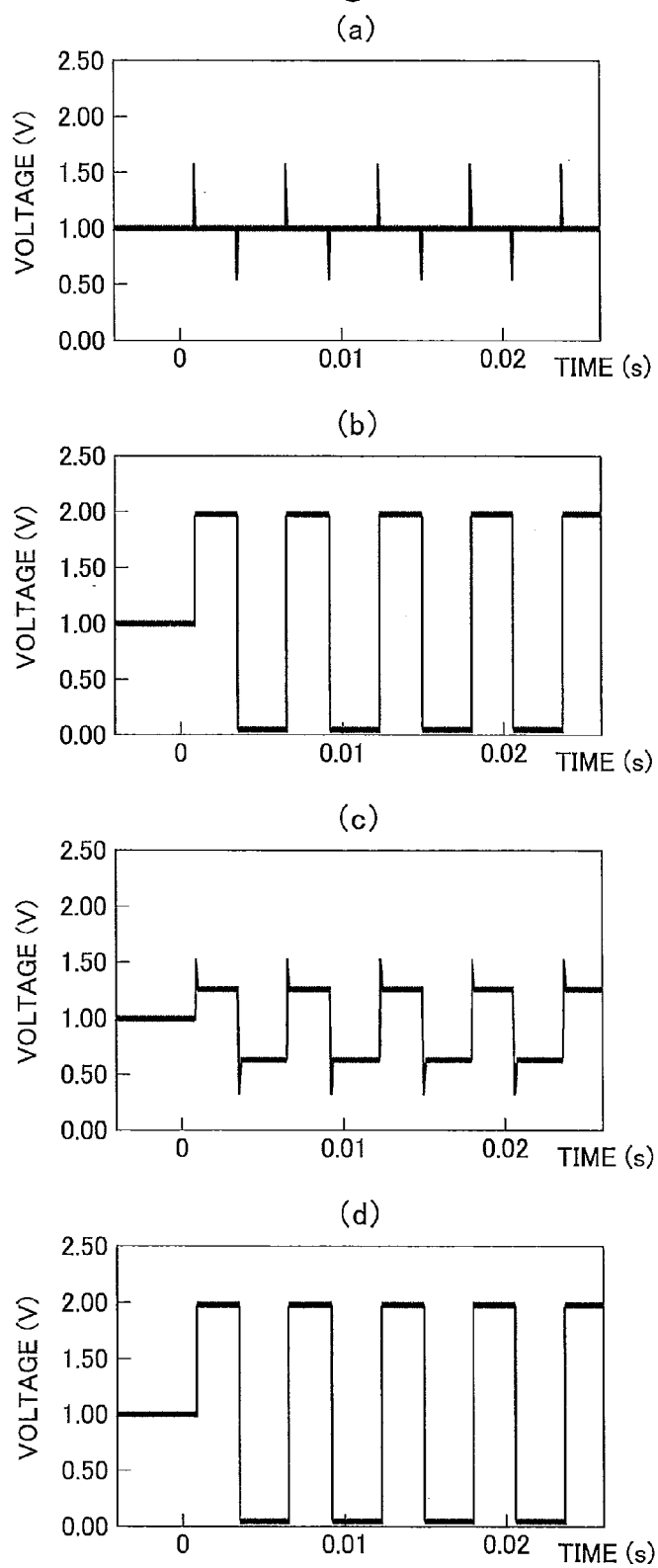
FIG. 9 is a graph showing the relationship between the voltages at points A and B in the circuit of FIG. 8, and time.

FIG. 9 shows the point-A voltage and the point-B voltage when the rectangular voltage applying means 303 has applied a pulse rectangular voltage switching between 2.0 V and 0 V at a cycle of 5.4 msec. FIG. 9(a) shows the voltage at point B (point-B voltage) when the electrochemical sensor 100 is in the normal state, FIG. 9(b) shows the voltage at point B (point-B voltage) when the electrochemical sensor 100 is in the completely dry state as the error state (the state in which the water in the water tank 20 is 0 cc and there is no moisture at all in the electrolyte layer 1), FIG. 9(c) shows the voltage at point B (point-B voltage) when the electrochemical sensor 100 had been in this completely dry state, then was kept at relative humidity 95% and atmospheric temperature 50° C. for 15 hours and recovered CO sensitivity, and FIG. 9(d) shows the voltage at point A (point-A voltage) corresponding to these FIGS. 9(a) to 9(c).

As shown in FIG. 9(a), the point-B voltage (normal voltage as a diagnosis indicator) in the normal state, that is, when there is enough moisture in the electrolyte layer 1 of the electrochemical sensor 100, shows a nearly constant level (about 1.0 V) when the rectangular voltage described earlier is applied. Applying the rectangular voltage (a pulse rectangular voltage switching between 2.0 V and 0 V at a cycle of 5.4 msec) apparently causes an alternating current corresponding to about 185 Hz to flow in the electrochemical sensor 100, which produces a level of resistance (corresponding to impedance) of the electrolyte of the electrochemical sensor 100 of about several Ω. Hence, the reason for the nearly constant voltage is that the resistance of the electrolyte of the electrochemical sensor 100 (about several Ω) is sufficiently lower than the 1 kΩ load resistor 301 so as to be irrelevant, and the voltage produced between A and B is about 1 V. The areas fluctuating to higher and lower voltages than 1 V in FIG. 9(a) are due to transitory phenomena when the application voltage is switched by the rectangular voltage applying means 303.

As shown in FIG. 9(b), the point-B voltage when the electrochemical sensor 100 is in the error state of the completely dry state; i.e., the water in the water tank 20 is 0 cc and there is no moisture at all in the electrolyte layer 1, appears as a virtually faithful reproduction of the rectangular voltage when the rectangular voltage described earlier is applied; that is, the point-B voltage shows a pulse rectangular voltage varying cyclically between 2.0 V and 0 V. This is because the resistance of the electrolyte of the electrochemical sensor 100 is several tens to several hundred kΩ as described earlier, hence the 1 kΩ of the load resistor 301 is sufficiently lower than the several tens to several hundred kΩ of resistance in the electrolyte so as to be irrelevant, and the voltage produced between A and B is about 0 V.

As shown in FIG. 9(c), in the case where a rectangular voltage is impressed, the point-B voltage when the electrochemical sensor 100 is in the desiccated state; i.e., when the water in the water tank 20 is 0 cc and a completely dry state in which there is no moisture at all in the electrolyte layer 1 is imminent, shows a pulse rectangular voltage varying cyclically between low and high voltages with less width of variation in voltage than in FIG. 9(b). For example, when the resistance of the electrolyte is 200Ω, the voltage is a pulse rectangular voltage varying cyclically between a low voltage of 0.83 V and a high voltage of 1.17 V, and when the resistance of the electrolyte is 300Ω, the voltage is a pulse rectangular voltage varying cyclically between a low voltage of 0.77 V and a high voltage of 1.23 V. This is because the resistance of the electrolyte of the electrochemical sensor 100 is 200 to 300Ω as described earlier, which resistance (200 to 300Ω) is 3/10 (when the resistance of the electrolyte is 300Ω) to 1/5 (when the resistance of the electrolyte is 200Ω) that of the 1 kΩ load resistor 301, and the voltage produced between A and B is 0.77 V (when the resistance of the electrolyte is 300Ω) to 0.83 V (when the resistance of the electrolyte is 200Ω).

Therefore, an error state as shown in FIGS. 9(b) and 9(c) can be diagnosed when the width of variation of the point-B voltage of the diagnostic apparatus 300 has increased to a level that is greater than or equal to a threshold (set proportionally to the level of the application voltage; for example, a width of variation of about ±0.2 V from a reference voltage of 1.0 V) relative to the normal voltage (1 V in FIG. 8) when the electrochemical sensor 100 is in the normal state (corresponding to an instance when the voltage is found to have increased relative to the normal voltage). Specifically, a completely dry state in which there is no moisture at all in the electrolyte layer 1, or a desiccated state in the process of leading to a state in which there is no moisture at all in the electrolyte layer 1, can be diagnosed as an error state; and a diagnosis of an error state due to a rise of the resistance in the electrolyte of the electrochemical sensor 100 can be reliably performed.

In particular, FIG. 9(c) shows a state in which the electrolyte layer 1 has no moisture at all, followed by a state in which humidity is kept at a high level (relative humidity: 95%), and is therefore believed to show the desiccated state that occurs in the process leading up to the state of a complete lack of moisture. Therefore, the diagnosing means 306 can diagnose an error state such as shown in FIG. 9(c), even if CO sensitivity is normal, when the width of variation of the point-B voltage of the diagnostic apparatus 300 has increased to greater than or equal to a threshold (set proportionally to the level of the application voltage; for example, a width of variation of about ±0.2 V from a reference voltage of 1.0 V) relative to the normal voltage (1 V in FIG. 8) when the electrochemical sensor 100 is in the normal state, and the width of variation is less than the point-B voltage in the completely dry state (±1.0 V in FIG. 8). Specifically, a desiccated state, which is in the process leading to a completely dry state in which there is no moisture at all in the electrolyte layer 1, can be diagnosed as an error state; and it can be diagnosed in a simple and reliable manner that an error state has occurred due to a rise of the resistance in the electrolyte of the electrochemical sensor 100. The normal voltage can be stored in advance in the memory means (not shown) in the diagnosing means 306.

Hence, according to the diagnostic method and diagnostic apparatus 300 of the electrochemical sensor 100 of the present application, it can be simply and reliably ascertained that the sensor is in a state where there is not enough moisture in the electrolyte layer 1 (desiccated state) and is in an error state due to a rise in the resistance in the electrolyte of the electrochemical sensor 100; and the electrochemical sensor 100 can be reliably replaced or otherwise attended to before any error is evident in the sensor output.

Other Embodiments (1) Although the apparatus in which the electrochemical sensor 100 is to be mounted when being diagnosed is not specified in the embodiments described earlier, it may be a gas alarm device demanding high reliability in detecting the concentration of a gas to be detected. Specifically, an alarm device offering increased reliability can be configured by effectively using the diagnostic method and diagnostic apparatus of the present application, with which it is possible to straightforwardly and reliably ascertain that a state in which the concentration of a gas to be detected cannot be accurately displayed is imminent.

(2) In cases when applying a pulse rectangular voltage (rectangular wave) is feasible in terms of the configuration in the second embodiment described earlier, a diagnosis may be made by applying an alternating voltage.

(3) In the first embodiment described earlier, whether or not a sensor is in an error state can be diagnosed on the basis of the impedance of the electrochemical sensor when an alternating current is impressed; and in the second embodiment described earlier, whether or not a sensor is in an error state can be diagnosed by intermittently detecting the impedance of the electrochemical sensor when an alternating current is impressed by detecting the output voltage of the electrochemical sensor when a pulse rectangular voltage is applied. Instead of these diagnostic means, however, an electrochemical sensor can also be diagnosed to be in an error state as follows.

Assuming that the resistance of the electrolyte has been calculated from the output voltage of an electrochemical sensor in a state in which an alternating current is impressed in the electrochemical sensor, whether or not the sensor is in an error state can be diagnosed on the basis of the output voltage of the electrochemical sensor to which the alternating current was applied. That is, in a state in which an alternating current has been impressed in the electrochemical sensor, the output voltage of the electrochemical sensor corresponds to the impedance of the electrochemical sensor. Therefore, in a state in which an alternating current has been impressed in the electrochemical sensor, the diagnosing means can diagnose that an electrochemical sensor is in an error state when it has been found that the output voltage of the electrochemical sensor is higher than the normal voltage, which is the output voltage when the electrochemical sensor is in the normal state (for example, when the output voltage has increased relative to the normal voltage by a set voltage or greater). The alternating current applied in this case may be, for example, an alternating current having a high frequency; i.e., 10 Hz or greater. The normal state of an electrochemical sensor is a state in which there is enough moisture in the electrolyte. Instead of the output voltage of the electrochemical sensor when an alternating current has been impressed, it is possible to make a diagnosis of an error state on the basis of the output current of the electrochemical sensor when an alternating current has been impressed, in a case where a decrease in the output current has been noted.

Assuming that the resistance of the electrolyte has been calculated from the output current of an electrochemical sensor in a state in which an alternating voltage has been applied to the electrochemical sensor, whether or not the sensor is in an error state can be diagnosed on the basis of the output current of the electrochemical sensor when the alternating voltage was applied. That is, in a state in which an alternating voltage has been applied to the electrochemical sensor, the output current of the electrochemical sensor corresponds to the impedance of the electrochemical sensor. Therefore, the diagnosing means can diagnose that an electrochemical sensor is in an error state when a decrease in the output current of the electrochemical sensor is found relative to the normal current, which is the output current when the electrochemical sensor is in the normal state (for example, when the output current has decreased relative to the normal current by a set voltage or greater). The alternating voltage applied in this case may be, for example, an alternating voltage having a high frequency; i.e., 10 Hz or greater. The normal state of an electrochemical sensor is a state in which there is enough moisture in the electrolyte. It is possible to make a diagnosis of an error state on the basis of the output voltage of the electrochemical sensor when an alternating voltage has been impressed instead of the output current of the electrochemical sensor when an alternating voltage has been applied, in a case where an increase in the output voltage has been noted.

(4) In the first embodiment and the other embodiment (3) described earlier, a pulse rectangular current can be used instead of an alternating current; moreover, the current is not limited to an alternating current or a pulse rectangular current, but may be other types of alternating currents that are not direct-current and that have a current varying cyclically over time. In the other embodiments (2) and (3) described earlier, a pulse rectangular voltage can be applied instead of an alternating voltage; moreover, the voltage is not limited to an alternating voltage or a pulse rectangular voltage, but may be other types of alternating voltages that are not direct-current voltages and that have a voltage varying cyclically over time.

The present invention can be effectively used as a method and apparatus for diagnosing an electrochemical sensor capable of simply and reliably diagnosing whether or not the sensor is in an error state due to a rise in the resistance in the electrolyte of an electrochemical sensor for detecting the concentration of a gas to be detected, on the basis of a current flowing between the sensing electrode and the opposite electrode or a voltage corresponding to this current.

[KEY]
1 ELECTROLYTE LAYER
2 ANODE (SENSING ELECTRODE)
3 CATHODE (OPPOSITE ELECTRODE)
11 SENSOR MEANS
20 WATER TANK
100 ELECTROCHEMICAL SENSOR
300 DIAGNOSTIC APPARATUS

What is claimed is:

1. A method for diagnosing an electrochemical sensor comprising a sensor unit including a solid or liquid electrolyte between a sensing electrode with which a gas to be detected makes contact and an opposite electrode, wherein the concentration of the gas to be detected is detected on the basis of a current flowing between the sensing electrode and the opposite electrode, or a voltage corresponding to the current, and wherein a water tank is connected to a lower part of the sensor unit for accommodating water or an absorbent polymer that has been caused to absorb water in an inner space thereof, the water present in the inner space being supplied to the electrolyte in the sensor unit, the method comprising the step of:
diagnosing whether or not the electrochemical sensor is in an error state representing a process of moving from a desiccated state in which there is no water at all in the water tank and there is not enough moisture in the electrolyte, to a completely dry state in which there is no moisture at all in the electrolyte when a resistance of the electrolyte is increased.

2. The method for diagnosing an electrochemical sensor of claim 1, further comprising the step of calculating the resistance of the electrolyte using an impedance of the electrochemical sensor in a state in which an alternating current or an alternating voltage has been applied in the electrochemical sensor; and
making a diagnosis that the electrochemical sensor is in the error state when there has been found an increase in impedance relative to a normal impedance, wherein the normal impedance is the impedance of the electrochemical sensor in a normal state.

3. The method for diagnosing an electrochemical sensor of claim 2, further comprising the step of calculating the impedance using an output voltage or an output current of the electrochemical sensor in a state where an alternating current has been applied in the electrochemical sensor; and making a diagnosis that the electrochemical sensor is in the error state in which there has been found an increase of impedance, when there has been found an increase of voltage relative to a normal voltage, wherein the normal voltage is the output voltage of the electrochemical sensor in the normal state, or when there has been found a decrease in current relative to a normal current, wherein the normal current is the output current of the electrochemical sensor in the normal state.

4. The method for diagnosing an electrochemical sensor of claim 3, further comprising the step of applying an alternating current having a frequency of 10 Hz or greater as the alternating current.

5. The method for diagnosing an electrochemical sensor of claim 2, further comprising the step of applying an alternating current having a frequency of 10 Hz or greater as the alternating current.

6. The method for diagnosing an electrochemical sensor of claim 2, further comprising the step of calculating the impedance using an output current or an output voltage of the electrochemical sensor in a state where an alternating voltage is applied to the electrochemical sensor; and making a diagnosis that the electrochemical sensor is in the error state in which there has been found an increase of impedance, when there has been found a decrease in current relative to a normal current, wherein the normal current is the output current of the electrochemical sensor in the normal state, or there has been found an increase of voltage relative to a normal voltage, wherein the normal voltage is the output voltage of the electrochemical sensor in the normal state.

7. The method for diagnosing an electrochemical sensor of claim 6, further comprising the step of applying an alternating voltage having a frequency of 10 Hz or greater as the alternating voltage.

8. The method for diagnosing an electrochemical sensor of claim 2, further comprising the step of applying an alternating voltage having a frequency of 10 Hz or greater as the alternating voltage.

9. An apparatus for diagnosing an electrochemical sensor comprising a sensor unit including a solid or liquid electrolyte between a sensing electrode with which a gas to be detected makes contact and an opposite electrode, wherein the concentration of the gas to be detected is detected on the basis of a current flowing between the sensing electrode and the opposite electrode, or a voltage corresponding to the current, and wherein a water tank is connected to a lower part of the sensor unit for accommodating water or an absorbent polymer that has been caused to absorb water in an inner space thereof, the water present in the inner space being supplied to the electrolyte in the sensor unit, the apparatus comprising:

detecting means for detecting a resistance of the electrolyte; and diagnosing means for diagnosing whether or not the electrochemical sensor is in an error state representing a process of moving from a desiccated state in which there is no water at all in the water tank and there is not enough moisture in the electrolyte, to a completely dry state in which there is no moisture at all in the electrolyte when the resistance of the electrolyte detected by the detecting means is increased.

10. The apparatus for diagnosing an electrochemical sensor of claim 9, wherein the resistance of the electrolyte is an impedance of the electrochemical sensor in a state where an alternating current or an alternating voltage has been applied in the electrochemical sensor; and the diagnosing means makes a diagnosis that the electrochemical sensor is in the error state when there has been found an increase of impedance relative to the normal impedance, wherein the normal impedance is the impedance of the electrochemical sensor in the normal state.

11. The apparatus for diagnosing an electrochemical sensor of claim 10, wherein the impedance is calculated using an output voltage or an output current of the electrochemical sensor in a state where an alternating current has been applied in the electrochemical sensor; and the diagnosing means makes a diagnosis that the electrochemical sensor is in the error state in which there has been found an increase of impedance, when there has been found an increase of voltage relative to a normal voltage, wherein the normal voltage is the output voltage of the electrochemical sensor in the normal state, or there has been found a decrease in current relative to a normal current, wherein the normal current is the output current of the electrochemical sensor in the normal state.

12. The apparatus for diagnosing an electrochemical sensor of claim 10, wherein the impedance is calculated using an output current or an output voltage of the electrochemical sensor in a state where an alternating voltage is applied to the electrochemical sensor; and the diagnosing means makes a diagnosis that the electrochemical sensor is in the error state in which there has been found an increase of impedance, when there has been found a decrease in current relative to a normal current, wherein the normal current is the output current of the electrochemical sensor in the normal state, or there has been found an increase of voltage relative to a normal voltage, wherein the normal voltage is the output voltage of the electrochemical sensor in the normal state.

* * * * *